(12) United States Patent
Schwertner et al.

(10) Patent No.: US 6,720,189 B1
(45) Date of Patent: Apr. 13, 2004

(54) BILIRUBIN TESTS AS RISK PREDICTORS FOR CANCER MORTALITY, RHEUMATOID ARTHRITIS, GILBERT'S SYNDROME AND ALL-CAUSE MORTALITY

(75) Inventors: Harvey A. Schwertner, Boerne, TX (US); Joseph R. Fischer, Jr., Boerne, TX (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 8 days.

(21) Appl. No.: 10/016,826

(22) Filed: Nov. 9, 2001

Related U.S. Application Data

(60) Provisional application No. 60/247,375, filed on Nov. 9, 2000, provisional application No. 60/247,376, filed on Nov. 9, 2000, and provisional application No. 60/247,377, filed on Nov. 9, 2000.

(51) Int. Cl.$^7$ ................................................ G01N 33/00

(52) U.S. Cl. ........................................................ 436/97

(58) Field of Search ................................ 436/63, 64, 97

(56) References Cited

U.S. PATENT DOCUMENTS 5,380,667 A * 1/1995 Schwertner .................. 436/71

OTHER PUBLICATIONS

Lakatos et al. "Serum Total, HDL, LDL CHolesterol, and Triglyceride Levels in Patients with Rheumatoid Arthritis", Clinical Biochemistry, vol. 21, pp. 93–96, Apr. 1988.*

* cited by examiner

*Primary Examiner*—Maureen M. Wallenhorst
(74) *Attorney, Agent, or Firm*—Frederic L. Sinder; Thomas L. Kundert

(57) ABSTRACT

A new method for predicting the risk of future cancer mortality, rheumatoid arthritis and all-cause mortality is disclosed. The method uses serum bilirubin levels as indicator for such risks, lower serum bilirubin levels generally indicating increased risk and higher levels a decreased risk.

1 Claim, 9 Drawing Sheets

| BASELINE CLINICAL CHARACTERISTICS OF STUDY PARTICIPANTS* | | | |
|---|---|---|---|
| CHARACTERISTICS | CONTROLS (n=414) | CASES (n=138) | P VALUE |
| Age (years) | 54.2±8.9 | 54.7±9.2 | NS |
| Bilirubin (mg/dL) | 0.80±0.24 | 0.66±0.24 | <0.001 |
| Exercise tolerance (METs) | 10.2±1.9 | 9.3±2.0 | <0.001 |
| BMI (kg/m$^2$) | 25.6±3.0 | 27.1±3.8 | <0.001 |
| Fasting glucose (mmol/L) | 5.7±1.0 | 6.0±1.3 | NS |
| Total cholesterol (mmol/L) | 5.8±0.9 | 5.8±1.1 | NS |
| Triglycerides (mmol/L) | 1.5±1.0 | 2.0±1.3 | <0.001 |
| DBP (mm Hg) | 82.1±10.5 | 82.7±10.7 | NS |
| SBP (mm Hg) | 127.5±18.8 | 127.3±17.1 | NS |
| Alcohol use (g/week) | 154.9±212.8 | 220.1±379.3 | 0.010 |
| Current smoking | 14% | 27% | <0.001 |
| Previous smoking# | 49% | 51% | NS |

*Values are given as mean ± SD. To convert values for cholesterol and triglycerides and bilirubin to mg/dL, multiply by 38.66 and 88.54, and 0.05847, respectively.
The percentages of previous smoking were calculated after patients with current smoking were excluded.

FIG. 1

RELATIVE RISKS AND 95% CONFIDENCE INTERVALS FOR CHD MORTALITY BY FOURTHS OF FASTING BILIRUBIN IN MEN

| | QUARTILE OF FASTING SERUM BILIRUBIN (mg/dL) (μmol/L) | | | | |
|---|---|---|---|---|---|
| | 1 (≤0.5) | 2 (0.51-0.70) | 3 (0.71-0.90) | 4 (>0.90) | P Trend |
| Cancer deaths (n=138) | 50 (36%) | 45 (33%) | 26 (19%) | 17 (12%) | |
| Controls (n=414) | 98 (24%) | 130 (31%) | 103 (25%) | 83 (20%) | |
| Crude analysis | | | | | |
| Relative risk | 1.0 | 0.70 | 0.54 | 0.44 | <0.001 |
| 95% CI | (reference) | (0.46-1.05) | (0.34-0.87) | 0.25-0.76 | |
| Multivariate analysis* | | | | | |
| Relative risk | 1.0 | 0.73 | 0.59 | 0.49 | <0.001 |
| 95% CI | (1.3-5.1) | (0.48-1.10) | (0.27-0.96) | 0.28-0.86 | |

*Adjustment for age, examination year, triglycerides, alcohol intake, previous smoking, current smoking, overweight, high cholesterol, hypertension, diabetes and low cardiorespiratory fitness.
(Dr Wei. Aren't bilirubin values in mg/dL??)

*FIG. 2*

RELATIVE RISKS FOR CANCER MORTALITY BY EACH MG/DL INCREASE IN FASTING BILIRUBIN IN MEN

| CATEGORY | Code | n | Relative risk and p-values | |
|---|---|---|---|---|
| | | | Univariate analysis | Multivariate analysis* |
| All-cancer mortality | 140-208 | 138 | 0.27  p<0.001 | 0.30  p<0.001 |
| Lung Cancer | 162 | 35 | 0.10  p<0.01 | 0.13  p<0.01 |
| Digestive cancer | 150-159 | 34 | 0.12  p<0.01 | 0.12  p<0.01 |
| Colorectal cancer | 153-154 | 13 | 0.07  p<0.05 | 0.07  p<0.05 |
| Prostate cancer | 185 | 10 | 0.10  p=0.12 | 0.11  p=0.15 |
| Bone&connective tissue cancer | 170-175 | 9 | 0.27  p=0.37 | 0.27  p=0.38 |
| Lymphatic&Hemotopoietic cancer | 200-208 | 27 | 0.38  p=0.19 | 0.44  p=0.27 |

*Adjustment for age, examination year, triglycerides, alcohol intake, previous smoking, current smoking, overweight, high cholesterol, hypertension, diabetes and low cardiorespiratory fitness.

FIG. 3

SERUM BILIRUBIN CONCENTRATIONS OF MALES AND FEMALES WITH RHEUMATOID ARTHRITIS

| | SEX | N | SERUM BILIRUBIN MEAN (SD)[1] | SERUM BILIRUBIN MEDIAN | P-VALUE | AGE |
|---|---|---|---|---|---|---|
| Rheumatoid arthritis[2] | M | 25 | 0.62 ± 0.33 | 0.53 | 0.003 | 65.4 ± 9.1 |
| Rheumatoid arthritis[2] | F | 20 | 0.47 ± 0.21 | 0.40 | 0.037 | 57.4 ± 7.5 |
| Rheumatology Service[3] | M | 48 | 0.62 ± 0.24 | 0.60 | 0.001 | 53.2 ± 15.0 |
| Rheumatology Service[3] | F | 103 | 0.47 ± 0.16 | 0.40 | 0.003 | 55.7 ± 16.2 |
| Rheumatoid arthritis[4] | M | 2 | 0.59 ± 0.06 | 0.59 | 0.52 | 58.0 ± 8.5 |
| Rheumatoid arthritis[4] | F | 12 | 0.433 ± 0.13 | 0.40 | 0.017 | 51.0 ± 11.3 |
| Controls | M | 129 | 0.83 ± 0.47 | 0.70 | | 32.0 ± 9.0 |
| Controls | F | 59 | 0.60 ± 0.40 | 0.60 | | 29.4 ± 9.2 |
| Outpatients | M | 3948 | 0.87 ± 1.24 | 0.7 | | 53.3 ± 19.1 |
| Outpatients | F | 3801 | 0.61 ± 0.84 | 0.5 | | 53.0 ± 18.9 |

[1] Serum bilirubin concentrations are expressed as mg/dL. To convert to μmole/L, divide by 0.05846. [2] Patients with rheumatoid arthritis. [3] Patients receiving treatment in Rheumatology Service. [4] Patients from the Rheumatology Service with diagnosed rheumatoid arthritis. Bilirubin concentrations of each group were compared to controls.

*FIG. 4*

SERUM BILIRUBIN CONCENTRATIONS OF PATIENTS WITH

DIFFERENT FORMS OF ARTHRITIS[1]

| TYPE OF ARTHRITIS | N | Female | N | Male |
|---|---|---|---|---|
| Rheumatoid arthritis | 20 | 0.47 ± 0.21 | 25 | 0.62 ± 0.33 |
| PSA | 6 | 0.50 ± 0.14 | 7 | 0.64 ± 0.16 |
| SLE | 9 | 0.47 ± 0.16 | 1 | 0.65 |

[1] Mean alanine transaminase and aspartate transaminase activities for males and females were 26.6 and 23.7 IU/L, respectively. Normal levels are 3 - 55 IU/L.

FIG. 5

DAY-TO-DAY VARIATION IN SERUM BILIRUBIN CONCENTRATIONS OF PATIENTS WITH RHEUMATOID ARTHRITIS

| PATIENT | SEX | DATES OF ANALYSIS | N | MEAN ± SD | CV |
|---|---|---|---|---|---|
| Patient 1 | Female | Jan89 - Mar89 | 13 | 0.41 ± 0.13 | 0.32 |
| Patient 1 | Female | Apr89-Nov89 | 24 | 0.43 ± 0.10 | 0.23 |
| Patient 1 | Female | Nov89 - May90 | 27 | 0.31 ± 0.14 | 0.45 |
| Patient 1 | Female | Jan91 - Nov91 | 27 | 0.37 ± 0.11 | 0.29 |
| Patient 1 | Female | Nov91 – Nov92 | 24 | 0.35 ± 0.13 | 0.37 |
| Patient 2 | Female | Aug91 – Dec92 | 15 | 0.23 ± 0.10 | 0.42 |
| Patient 3 | Male | Jan88 – Jul88 | 26 | 0.27 ± 0.10 | 0.38 |
| Patient 3 | Male | Sep88 – Apr90 | 27 | 0.29 ± 0.11 | 0.39 |
| Patient 3 | Male | Apr90 – Dec90 | 27 | 0.33 ± 0.13 | 0.40 |
| Patient 3 | Male | Feb91 – Nov92 | 26 | 0.53 ± 0.17 | 0.31 |

*FIG. 6*

DAY-TO-DAY VARIATION IN SERUM BILIRUBIN

CONCENTRATIONS OF PATIENTS WITH RHEUMATOID ARTHRITIS

| Patient 1 Jan89-Mar89 Female | Patient 1 Nov89-May90 Female | Patient 1 Jan91-Nov91 Female | Patient 1 Nov91-Nov92 Female | Patient 2 Aug91-Dec92 Male | Patient 3 Jan88-Jul88 Male | Patient 3 Sep88-Apr90 Male | Patient 3 Apr90-Dec90 Male | Patient 3 Feb91-Nov92 Male |
|---|---|---|---|---|---|---|---|---|
| 0.3 | 0.3 | 0.2 | 0.4 | 0.2 | 0.3 | 0.5 | 0.3 | 0.6 |
| 0.5 | 0.3 | 0.4 | 0.6 | 0.2 | 0.2 | 0.5 | 0.4 | 0.8 |
| 0.3 | 0.4 | 0.4 | 0.5 | 0.1 | 0.3 | 0.1 | 0.1 | 0.8 |
| 0.3 | 0.3 | 0.3 | 0.5 | 0.3 | 0.2 | 0.3 | 0.4 | 0.5 |
| 0.5 | 0.2 | 0.5 | 0.3 | 0.3 | 0.2 | 0.3 | 0.6 | 0.6 |
| 0.6 | 0.5 | 0.4 | 0.4 | 0.2 | 0.2 | 0.2 | 0.5 | 0.7 |
| 0.3 | 0.2 | 0.3 | 0.2 | 0.3 | 0.5 | 0.3 | 0.3 | 0.6 |
| 0.5 | 0.5 | 0.3 | 0.4 | 0.3 | 0.3 | 0.2 | 0.4 | 0.4 |
| 0.3 | 0.3 | 0.3 | 0.4 | 0.2 | 0.2 | 0.3 | 0.2 | 0.5 |
| 0.2 | 0.3 | 0.3 | 0.4 | 0.2 | 0.3 | 0.1 | 0.4 | 0.5 |
| 0.5 | 0.1 | 0.5 | 0.4 | 0.5 | 0.5 | 0.5 | 0.4 | 0.5 |
| 0.4 | 0.5 | 0.3 | 0.4 | 0.2 | 0.2 | 0.2 | 0.1 | 0.7 |
| 0.6 | 0.2 | 0.4 | 0.3 | 0.1 | 0.2 | 0.3 | 0.3 | 0.5 |
|  | 0.1 | 0.3 | 0.1 | 0.2 | 0.1 | 0.3 | 0.2 | 0.6 |
|  | 0.4 | 0.4 | 0.4 | 0.2 | 0.3 | 0.3 | 0.2 | 0.5 |
|  | 0.2 | 0.4 | 0.3 |  | 0.2 | 0.4 | 0.3 | 0.6 |
|  | 0.5 | 0.4 | 0.4 |  | 0.2 | 0.2 | 0.4 | 0.3 |
|  | 0.2 | 0.2 | 0.5 |  | 0.2 | 0.2 | 0.1 | 0.6 |
|  | 0.1 | 0.7 | 0.4 |  | 0.4 | 0.4 | 0.4 | 0.7 |
|  | 0.4 | 0.4 | 0.3 |  | 0.3 | 0.2 | 0.6 | 0.1 |
|  | 0.2 | 0.2 | 0.3 |  | 0.3 | 0.5 | 0.3 | 0.5 |
|  | 0.1 | 0.4 | 0.1 |  | 0.5 | 0.3 | 0.4 | 0.4 |
|  | 0.5 | 0.5 | 0.3 |  | 0.2 | 0.2 | 0.2 | 0.3 |
|  | 0.3 | 0.4 | 0.1 |  | 0.3 | 0.3 | 0.2 | 0.4 |
|  | 0.4 | 0.3 |  |  | 0.3 | 0.3 | 0.5 | 0.4 |
|  | 0.5 | 0.3 |  |  | 0.2 | 0.2 | 0.3 | 0.5 |
|  | 0.5 | 0.4 |  |  |  |  | 0.3 | 0.4 |

| N | | | | | | | | |
|---|---|---|---|---|---|---|---|---|
| 13 | 27 | 27 | 24 | 15 | 26 | 27 | 27 | 26 |

| Mean ± SD | | | | | | | | |
|---|---|---|---|---|---|---|---|---|
| 0.41 ± 0.13 | 0.32 ± 0.14 | 0.37 ± 0.11 | 0.35 ± 0.13 | 0.23 ± 0.10 | 0.27 ± 0.10 | 0.29 ± 0.11 | 0.33 ± 0.13 | 0.53 ± 0.17 |

| Inter-day coefficient of variation | | | | | | | | |
|---|---|---|---|---|---|---|---|---|
| 0.32 | 0.46 | 0.29 | 0.37 | 0.42 | 0.36 | 0.39 | 0.40 | 0.31 |

*FIG. 7*

| BASELINE CLINICAL CHARACTERISTICS OF STUDY PARTICIPANTS* | | | |
|---|---|---|---|
| CHARACTERISTICS | Controls (n=839) | CASES (n=385) | P VALUE |
| Age (years) | 51.5±10.4 | 52.4±9.1 | NS |
| Bilirubin (mg/dl) | 7.6±0.3 | 6.5±0.3 | <0.001 |
| Total cholesterol (mmol/L) | 5.7±0.9 | 6.0±1.2 | <0.001 |
| Triglycerides (mmol/L) | 1.5±1.3 | 1.9±1.4 | <0.001 |
| BMI (kg/m$^2$) | 25.8±3.1 | 26.7±3.7 | <0.001 |
| DBP (mm Hg) | 81.7±9.9 | 85.1±12.1 | <0.001 |
| SBP (mm Hg) | 124.9±15.2 | 130.9±19.7 | <0.001 |
| Alcohol use (g/week) | 185.6±286.5 | 163.5±290.8 | NS |
| Abnormal resting or exercise ECG | 15% | 30% | <0.001 |
| Diabetes | 7% | 17% | <0.001 |
| Current smoking | 14% | 21% | <0.001 |
| Family history of cardiovascular disease | 35% | 35% | NS |

*Values are given as mean ± SD. To convert values for cholesterol, triglycerides, and bilirubin to mg/dL, multiply by 38.66, 88.54, and 0.05847, respectively.
Are the bilirubin values correct or should they be 0.65 ± 0.03, etc?

*FIG. 8*

RELATIVE RISKS AND 95% CONFIDENCE INTERVALS FOR MORTALITY BY FASTING SERUM BILIRUBIN IN MEN

| | QUARTILE OF FASTING SERUM BILIRUBIN (mg/dl) | | | |
|---|---|---|---|---|
| | 1 (<0.5) | 2 (0.5-1.0) | 3 (>1.0) | p-values |
| All-cause deaths (n=385) | 83 (21.6%) | 265 (68.8%) | 37 (9.6%) | |
| Controls (n=839) | 126 (15.0%) | 593 (70.7%) | 120 (14.3%) | |
| Age and examination-year adjusted analysis* | | | | |
| Relative risk | 1.0 | 0.68 | 0.51 | <0.0001 |
| 95% CI | (reference) | (0.53-0.87) | (0.35-0.77) | |
| Multivariate analysis† | | | | |
| Relative risk | 1.0 | 0.76 | 0.59 | <0.0001 |
| 95% CI | (reference) | (0.59-0.98) | (0.40-0.87) | |

*Adjustment for age and examination year.
†Adjustment for age, examination year, parental CVD, high cholesterol, current smoking, diabetes mellitus, triglycerides, alcohol intake, hypertension, current smoking, overweight, and abnormal resting and exercise ECG.

*FIG. 9*

BILIRUBIN TESTS AS RISK PREDICTORS FOR CANCER MORTALITY, RHEUMATOID ARTHRITIS, GILBERT'S SYNDROME AND ALL-CAUSE MORTALITY

CROSS-REFERENCE TO RELATED APPLICATIONS

This application claims priority under 35 U.S.C. § 119(e) from U.S. provisional application No. 60/247,375, filed Nov. 9, 2000 by Harvey A. Schwertner, Ming Wei, Larry W. Gibbons, Tedd L. Michell and Stephen N. Blair, titled Protective Effect of Elevated Bilirubin or Serum Bilirubin Concentrations on Patients with Gilbert's Syndrome; No. 60/247,376, filed Nov. 9, 2000 by Harvey A. Schwertner, Ming Wei, Larry W. Gibbons, Stephen N. Blair and Qintian Zheng, titled Low Fasting Serum Bilirubin as a Predictor of Cancer Mortality; and, No. 60/247,377, filed on Nov. 9, 2000 by Harvey A. Schwertner, Robert Kisselburgh and Joseph R. Fischer, Jr., titled Low Serum Bilirubin Antioxidate Concentrations as a Factor for Rheumatoid Arthritis.

This application is related to U.S. application Ser. No. 10/016,825, filed Nov. 9, 2001 by Harvey A. Schwertner and Joseph R. Fischer, Jr., titled Combined Cholesterol And Bilirubin Tests As Risk Predictors For Coronary Artery Disease, the invention description of which is incorporated by reference into this application. U.S. application Ser. No. 10/016,825 and this application are based on a related series of studies of the utility of bilirubin tests as a risk predictor for various diseases.

RIGHTS OF THE GOVERNMENT

The invention described herein may be manufactured and used by or for the Government of the United States for all governmental purposes without the payment of any royalty.

BACKGROUND OF THE INVENTION

The present invention relates generally to predictive tests for determining the risk of future onset of various diseases and, in one example of the invention, a related test for determining a reduced probability for the future onset of various diseases and early all-cause mortality, and more particularly to the use of serum bilirubin tests and the serum concentration levels of serum bilirubin as risk predictors.

This invention builds on the teachings of U.S. Pat. No. 5,380,667, issued Jan. 10, 1995, to Harvey A. Schwertner, a co-inventor of the present invention, titled Serum Bilirubin and Liver Function Tests as Risk Predictors for Coronary Artery Disease, the invention description of which is incorporated by reference into this description.

U.S. Pat. No. 5,380,667 showed new non-lipid risk factors for predicting coronary heart disease, most specifically that subacute levels of serum total bilirubin are a significant independent risk predictor for coronary artery disease (CAD). The patent also showed that the ratio of total cholesterol to bilirubin may be used in place of HDL-cholesterol or the ratio of total cholesterol to HDL-cholesterol as a predictor for CAD.

The present invention is the result of additional studies involving bilirubin concentrations that reveal other predictive abilities for various diseases.

There is always a need for new risk factors and other predictive tests for disease and even, as demonstrated by one example of the present invention, for tests that may predict a lowered risk for various diseases and even a lowered risk for early onset of all-cause mortality.

It is, therefore, a principal object of the present invention to provide new risk factors and other predictive tests for disease utilizing tests for bilirubin.

It is a feature of the present invention that it uses information generally already available from tests already routinely performed.

It is another feature of the present invention that it can be used to diagnose health or the absence of disease.

It is an advantage of the present invention that it improves specificity, sensitivity and accuracy of predictive tests for various diseases.

It is another advantage of the present invention that its use will result in fewer false predictions.

It is yet another advantage of the present invention that its use will result in treatment for individuals with various diseases to begin at an earlier age.

It is a further advantage of the present invention that tests for bilirubin concentrations are easier and cheaper to perform than many other predictive tests for the same diseases.

These and other objects, features and advantages of the present invention will become apparent as the description of certain representative embodiments proceeds.

SUMMARY OF THE INVENTION

The present invention provides new risk factors for predicting the risk of various diseases. The unique discovery of the present invention is that subacute levels of serum total bilirubin is a significant independent risk predictor for various diseases.

Accordingly, the present invention is directed to a method for characterizing the risk of future cancer mortality for an individual, comprising the steps of obtaining the level of the patient's serum total bilirubin; comparing the obtained level to a predetermined level for serum total bilirubin; and, characterizing from the comparison the risk of future cancer mortality for the individual. The predetermined level of serum total bilirubin may be 0.66 mg/dl, wherein levels near or below 0.66 mg/dl indicate that the individual has a higher than normal risk of future cancer mortality.

The present invention is also directed to a method for characterizing the risk of rheumatoid arthritis for an individual, comprising the steps of obtaining the level of the individual's serum total bilirubin; comparing the obtained level to a threshold level for serum total bilirubin; and, characterizing from the comparison the risk of rheumatoid arthritis for the individual.

The present invention is further directed to a method for characterizing the reduced probability of future cardiovascular disease, future cardiovascular mortality, future cancer mortality and future all-cause mortality for an individual, comprising the steps of obtaining the level of the individual's serum total bilirubin; comparing the obtained level to a predetermined level for serum total bilirubin; and, characterizing from the comparison a reduced probability for future cardiovascular disease, future cardiovascular mortality, future cancer mortality and future all-cause mortality for the individual.

DESCRIPTION OF THE DRAWINGS

The present invention will be more clearly understood from a reading of the following detailed description in conjunction with the accompanying drawings.

FIG. 1 is a table showing the baseline clinical characteristics of participants in the study underlying the cancer mortality example of the present invention.

FIG. 2 is a table showing relative risks and 95% confidence intervals for CHD mortality by fourths of fasting bilirubin in men.

FIG. 3 is a table showing the relative risks for cancer mortality by each mg/dl increase in fasting bilirubin in men.

FIG. 4 is a table showing the serum bilirubin concentrations of males and females with rheumatoid arthritis.

FIG. 5 is a table showing the serum bilirubin concentrations of patients with different forms of arthritis.

FIG. 6 is a table showing the day-to-day variations in serum bilirubin concentrations of patients with rheumatoid arthritis.

FIG. 7 is another table showing the day-to-day variations in serum bilirubin concentrations of patients with rheumatoid arthritis.

FIG. 8 is a table showing the baseline clinical characteristics of study participants of serum bilirubin concentrations of patients in the study underlying the protective effects of elevated bilirubin and Gilbert's syndrome example of the present invention.

FIG. 9 is a table showing the relative risks and 95% confidence intervals for mortality by fasting serum bilirubin in men.

DETAILED DESCRIPTION

Cancer Mortality

In vitro, bilirubin is a strong antioxidant and protects cells from oxidative injury, but in vivo its function remains to be determined. This example of the present invention is the result of a study to determine if low serum bilirubin might be associated with an increased risk of cancer mortality and if elevated levels are associated with a decreased risk. Serum bilirubin has been shown to act as a natural antioxidant and to protect cells from oxidative injury in vitro. Serum bilirubin has been shown to protect many kinds of cells from injury in vitro, however, no study has been performed to investigate the association between serum bilirubin and cancer.

Study Methods

A prospective nested case-control study was used to determine if baseline fasting serum bilirubin concentrations predict future cancer mortality. Data were obtained from an 11-year follow-up study of 17,332 men without known cancer at baseline. Fasting serum bilirubin concentrations of 138 men who subsequently died from cancer were compared with 414 age-matched 414 men who were randomly chosen from survivors.

Findings

Baseline fasting serum bilirubin concentrations were inversely associated with future cancer mortality. The means of baseline fasting serum bilirubin concentration was 0.66 mg/dL for men with cancer deaths and 0.80 mg/dL for the controls (P<0.001). Those in the highest quartile of bilirubin had a 0.44-fold lower risk of cancer mortality (95% confidence interval:0.25–0.76) than compared to those in the lowest quartile. A dose-response association between serum bilirubin and cancer mortality also was found (p<0.001). The results remained significant after adjustment for age, examination year, overweight, cigarette smoking, alcohol consumption, triglyceride, cardiorespiratory fitness, high cholesterol, hypertension and diabetes. Similar associations were found when lung cancer, colorectal cancer and prostate cancer were examined separately.

Conclusions

In data from a prospective study, baseline fasting serum bilirubin was found to be a strong predictor of future cancer mortality.

Serum bilirubin is derived primarily from the degradation of hemoglobin and is the major end product of heme catabolism. In clinical medicine, high concentrations of bilirubin usually serve as an index of hepatic and billiary disease, whereas low concentrations are considered to be normal and to signify health. Many studies have demonstrated that bilirubin protects cells from oxidative injury in vitro. It has been suggested that because non-lethal genetic damage appears to account for some forms of carcinogenesis, elevated serum bilirubin might be associated with a low risk of cancer and low concentrations might be associated with an increased risk of cancer, so that bilirubin may have potential effect on cancer protection. An association between serum bilirubin and cancer had not been previously reported in the literature, nor had serum bilirubin been identified as a possible risk factor for cancer mortality.

The present invention results from an investigation and determination of whether baseline fasting serum bilirubin concentrations are associated with all-cancer mortality prevalence. In addition, the present invention results from an investigation of the association between serum bilirubin concentrations and colorectal cancer, lung cancer and prostate cancer mortality.

Study Methods

Patients

Cancer mortality was based on data on risk factors and cancer mortality and were obtained from the Aerobics Center Longitudinal Study (ACLS). Case and controls were selected from 17,332 men with who underwent baseline examinations during the interval from 1970 to 1986 and who were followed up to the end of 1989. Study participants came to the clinic for periodic health examinations and counseling about diet, exercise and other lifestyle factors associated with increased risk of chronic disease. Patients with a history of cancer or cardiovascular disease at baseline were excluded from this study.

The study has been reviewed and approved annually by the Cooper Institute Institutional Review Board. All patients gave their informed consent to participate in the examination and in the follow-up study. They completed a health and medical history and underwent a physical examination by a clinic physician that included measurement of height and weight, blood chemistry analyses, measurement of blood pressure, a resting electrocardiogram (ECG), and a maximal exercise treadmill test. Trained technicians conducted all examinations and interviews following procedures described in a detailed operations manual using procedures described in a detailed manual of operations conducted all examinations and interviews. The examination procedures have been described in greater detail in several prior publications.{190} {189}

Clinical Measurements

Technicians measured height and weight with a standard physician's balance beam scale and stadiometer. Body mass index (BMI) was calculated by dividing the weight (kg) by the square of the height (m$^2$) as kg/m$^2$. Trained technicians measured blood pressure with mercury sphygmomanometers following the American Heart Association recommendations. Blood pressure readings were taken with a mercury sphygmomanometers following the American Heart Association recommendations. The lowest of the three values were used for the statistical analyses. Blood pressures were measured three times, with the lowest of the three values used in analyses.

Laboratory Analyses

Blood samples for biochemical analyses were drawn from the antecubital vein by standard venipuncture techniques. The samples were obtained between 7 and 8 A.M. following an overnight fast of 12–14 hours. Total serum bilirubin from non-hemolyzed serum was analyzed with a commercial calorimetric method using diazotized sulfanilic reagent. To assess intra-patient variability in serum bilirubin, the bilirubin measurements of bilirubin in 20 patients were repeated. The two bilirubin values were found to be identical for each of the 20 patients ($r^2=1.00$). The laboratory participates in intra- and inter-laboratory quality control programs sponsored by the Centers for Disease Control and Prevention (CDC) Lipid Standardization Program.

Mortality Surveillance

The principal method of mortality surveillance was by the National Death Index (NDI), which has been validated and widely used in population-based cohort studies. Nosologists coded the death certificates according to the International Classification of Diseases, Ninth Edition, Revised for the underlying and up to four contributing causes of death. Cancer mortality (International Classifications of Diseases, Ninth Edition, Revised codes 140–208) was the primary outcome variable used in this report. Also identified were lung cancer (code 162), prostate cancer (code 185) and colorectal cancer (code 153–154).

For this analysis, case subjects were those who died from cancer during follow-up. Three control subjects for each case were selected randomly from among survivors who met the matching criterion of age (±5 years). Using this method, 138 cancer deaths and 414 controls were evaluated in a prospective case-control study.

Statistical Analysis

The patients were considered to have a high serum cholesterol if their cholesterol concentration was >6.2 mmol/L (>240 mg/dL). Hypertension was defined as a history of physician-diagnosed hypertension or blood pressure ≧140/90 mm Hg at the clinical examination. Diabetes was considered to be present if the patient had a history of diabetes, a history of insulin use, or a fasting plasma glucose ≧7.0 mmol/L (≧126 mg/dL). Current cigarette smoking was defined as self-reported "smoking now" at baseline. Overweight was defined as a BMI ≧25 and low cardiorespiratory fitness as the least fit 20% in each age group. Alcohol intake was determined by self-reported alcohol consumption. Alcohol consumption was estimated as 1.1 grams for 1 ounce of beer, 2.7 grams for 1 ounce of wine, and 15.1 grams for 1 ounce of liquor reported on the medical history questionnaire.

Conditional logistic-regression models were used that accounted for other potential variables to provide point and 95% confidence interval estimates. All reported P values are 2-sided.

Results

Baseline clinical characteristics of the 138 subjects who subsequently died from cancer and the 414 matched survivors are given in FIG. 1. Both cases and controls were free of known cancer at baseline and were similar in age. The subjects who subsequently died from cancer were found to have baseline serum bilirubin concentrations that were significantly lower than those of the survivors (0.80 versus 0.66 mg/dl; P<0.001). Cases had higher levels of triglycerides, body mass index, prevalence of current cigarette smoking and alcohol intake, but lower exercise tolerance scores than did the controls. The cases also had lower exercise tolerance scores at baseline than did the controls.

To determine if differences in baseline serum bilirubin concentrations between cases (cancer deaths) and controls are independent of other the potential risk factors, baseline bilirubin concentrations were determined and checked for cases and controls for each of the potential risk factor categories: triglycerides (>2 mmol/l or otherwise), body mass index>25 or otherwise; current cigarette smoking, previous smoking, or non-smoking; alcohol consumers or non-drinkers; men with high or low exercise tolerance scores. The inverse association between serum bilirubin and cancer mortality was found to persistent across each of these subgroups those subgroup analyses (table not shown).

To estimate the association of different bilirubin levels and future to cancer risk, control subjects were categorized by quartiles of baseline serum bilirubin concentration. The distribution of study subjects in cases and controls for each bilirubin quartile is shown in FIG. 2. Because of the uneven distribution of bilirubin concentrations, each quartile did not contain exactly 25 percent of the controls. The relative risks of future cancer death were decreased progressively lower with each higher levels of as the baseline fasting serum bilirubin concentrations increased. When compared with to men with in the lowest quartile (bilirubin 0.5 mg/dl or less), men in the highest quartile (bilirubin>0.9 mg/dl) had a relative risk of 0.44 0.49 (95% CI: 0.28–0.86) for cancer mortality after adjustment for cigarette smoking, age, examination year, low cardiorespiratory fitness, overweight, triglyceride, cardiorespiratory fitness, and alcohol consumption, as shown in FIG. 2. Because cigarette smoking could be a major confounder in this study, analyses were performed after adjusting for used the number of cigarettes smoked and pack-years of smoking. The association between bilirubin and cancer mortality remained unchanged after adjustment of these potential confounders. Other influential factors were considered such as vitamin intake, serum albumin, white blood cell count, hematocrit and hemoglobin, and liver function. The association between serum bilirubin and cancer mortality changed little or remained unchanged when these factors were examined.

The inverse association between bilirubin as a continuous variable and cancer mortality is shown in FIG. 3. Conditional logistic-regression models were used that accounted for other potential variables to provide relative risk estimates for cancer mortality of reach for each 1 mg/dL increase in bilirubin for cancer mortality. After adjustment for other about potential risk factors, each mg/dL increment of bilirubin was associated with a 70% (95% CI: 40%–85%, p<0.001) decrease in risk of all-cancer mortality. A similar tendency was present found in the association between when bilirubin and the three major cancers for men were examined, i.e., lung cancer, prostate cancer and colorectal cancer. The association of bilirubin and with prostate cancer, however, was not statistically significant as shown in FIG. 3.

Discussion

An unexpected inverse association was discovered between baseline fasting serum bilirubin and risk of future cancer mortality. Low baseline fasting serum bilirubin concentrations are associated with an increased the risk of cancer mortality. This association persisted after adjustment for cigarette smoking and other potential confounders. In addition, men with low levels of serum bilirubin are at a higher risk of developing a wide range of cancer including lung cancer and colorectal cancer.

It is not known why serum bilirubin is inversely associated with future cancer mortality. The mechanism of for the inverse association between serum bilirubin and cancer mortality remains to be determined is unclear. It is not known if elevated Bilirubin could possibly be protecting cells from genetic damage and from other forms of oxidative stress that could result in an increased incidence of cancer. Alternatively, bilirubin could be a marker for another true risk factor. A number of studies, however, have shown that bilirubin can protect cells from injury in vitro. This cytoprotective effect of bilirubin for has been repeatedly demonstrated in many laboratory studies and with many cell types, e.g., hepatocytes, erythrocytes, myocytes and neurons. Bilirubin also has been shown to be strong inhibitor of peroxyl radicals generated chemically in either homogeneous solution and in multilamellular liposomes, in vitro. Based on the findings that bilirubin efficiently changed inhibited peroxyl radicals generated chemically in either homogenous solution or multilamellular liposomes, in vitro, other researchers have hypothesized that bilirubin might act as a potent biological chain-breaking antioxidant. It is well known that non-lethal genetic damage is at the center of carcinogenesis. Such genetic damage (or mutation) might be acquired by the action of external environmental agents and or by internal toxic agents.

In this study, blood samples were collected under uniform fasting conditions and at standardized fasting times. Since both dietary composition and total caloric intake appear to have an acute effect on bilirubin levels, fasting conditions might minimize this source of biological variability in bilirubin concentrations. Certainly the conditions under which blood is drawn need to be standardized in order to get reproducible results. One advantage of this study was using standard fasting procedure with similar fasting times in each individual.

The limitations of the study population must be taken into consideration. The subjects in this report, for example, were all men and most (97%) were white. They were also from the middle and upper socioeconomic class. In spite of this, previous studies by various co-inventors have shown that the risk factors for cardiovascular disease, diabetes and all-cause mortality are similar to those found for other populations. While it remains to be determined if these results apply to women and to individuals of other races, such a relationship will reasonably be expected by those of ordinary skill in the art of the invention. Diet and vitamins intake were self-reported and were only reported for one time in this study. However, when a study was performed using three-day diet records, no nutritional components in diet which were associated with fasting serum bilirubin were found. In addition, it was found that vitamin intake did not have any effect on fasting serum bilirubin.

In conclusion, fasting serum bilirubin concentrations have been found to be inversely associated with all-cancer mortality. Because the measurement of serum bilirubin is a routine practice in clinical laboratory, it may add important information for cancer risk classification. Further large prospective studies are needed to investigate and study the association of which specific bilirubin component is most closely associated with of bilirubin and a decreased risk of cancer and cancer mortality. Both in vitro and in vivo experimental studies identify mechanisms by which bilirubin exerts its protective effect. Such studies may lead to prevention, early diagnosis and therapeutic approaches for cancer prevention, and may also provide important insight into the underlying mechanisms of the association and may lead to a prevention, early diagnosis and therapy for cancer.

Rheumatoid Arthritis

Background

Bilirubin has antioxidant, anti-inflammatory and cytoprotective properties. This example of the present invention results from a study to investigate and determine if serum bilirubin concentrations are decreased in individuals with rheumatoid arthritis.

Study Methods

A case control study of serum bilirubin concentrations was performed in 25 men and 20 women with rheumatoid arthritis and 129 men and 99 women without arthritis. In addition, bilirubin concentrations were determined of 48 men and 103 women who were receiving treatment in the rheumatology service for undefined arthritic diseases.

Results

Serum bilirubin concentrations were lower for men and women with rheumatoid arthritis than for men and women without rheumatoid arthritis ($p<0.003$ and $0.037$, respectively). The serum bilirubin concentrations of men and women attending the rheumatology service were also lower than that of the men and women in the control group ($p<0.001$ and $P<0.003$, respectively). In addition, low serum bilirubin concentrations were found for patients with systemic lupus erythematosus and psoriatic arthritis. The low bilirubin concentrations were found to persist over a 5 month to 4 year follow-up period and were independent of serum albumin concentrations and alanine and aspartate transaminase activities.

Conclusions

Patients with rheumatoid arthritis were found to have chronic low bilirubin concentrations. The results show that low serum bilirubin levels may be a risk factor for rheumatoid arthritis and that mildly elevated levels may be protective against rheumatoid arthritis.

Introduction

Rheumatoid arthritis (RA) is a painful, incapacitating disease of the joints that affects all age groups both as a chronic and as an acute disorder. The factors responsible for the damaging effects of rheumatoid arthritis are not known. However, autoimmune and oxidative processes appear to be involved. A number of studies have shown that serum malondialdehyde and other lipid peroxidation products are increased in patients with RA. Less information, however, is available on the concentrations of specific antioxidants. In one study, the levels of $\alpha$-tocopherol and $\beta$-carotene were shown to be decreased, however, in another study, no differences in the two antioxidants were found. In other studies, erythrocyte glutathione and plasma ceruloplasmin concentrations were elevated in individuals with RA.

It is generally accepted that oxidative reactions are involved in the pathophysiology of many degenerative disease processes including rheumatoid arthritis, diabetes, cancer and cataracts. Changes in bilirubin concentrations in these diseases, however, have not been determined. A previous invention of one of the co-inventors found a significant association between low, but yet normal, serum bilirubin concentrations and coronary artery disease (CAD). This appears to have been the first finding of a relationship between a low, but yet normal, serum bilirubin concentration and a specific disease. It is not known why bilirubin concentrations are lower in individuals with CAD than in individuals without CAD, nor is it known if low bilirubin concentrations are associated with other diseases and medical conditions. It may be postulated, however, that serum bilirubin may be acting as an antioxidant and that the lower concentrations may be a reflection of increased oxidation of bilirubin.

Bilirubin has been shown to act as a powerful antioxidant and as an anti-inflammatory agent in several in vitro systems and to have cytoprotective properties. It also has been shown to be more efficient at inhibiting free radicals than α-tocopherol and to be more effective as a cytoprotective agent than either vitamin E or vitamin C. It is not clear how much of the antioxidant activity of serum is attributed to bilirubin, however, several recent studies indicate that it is among the most powerful antioxidants in serum. An involvement of bilirubin in immune reactions and inflammatory processes has also been documented. Increased heme oxygenase activity, which results in higher bilirubin concentrations, has been linked to a faster resolution of inflammation whereas an inhibition of this enzyme appears to enhance the inflammatory process. In addition, recent studies have shown that the polyphenolic fraction from green tea, which has both antioxidant and anti-inflammatory properties, substantially decreases collagen induced arthritis in mice.

This example of the present invention results from a study to further clarify the antioxidant status of patients with rheumatoid arthritis. The serum bilirubin antioxidant concentrations of patients with and without rheumatoid arthritis were specifically examined as well as in individuals with systemic lupus and psoriatic arthritis (PSA). In addition, a study was made to determine if serum bilirubin concentrations change over time.

Study Materials and Methods

Study Populations

The study population consisted of active duty or retired military members and their dependents who were receiving medical care in the rheumatology service or in other outpatient services. The group with rheumatoid arthritis consisted of 25 men and 20 women and the group receiving treatment in the rheumatology service consisted of 48 men and 103 women. The serum bilirubin concentrations were also determined on a subgroup of patients in the rheumatology service who were identified as having rheumatoid arthritis. The control group consisted of 129 men and 99 women who were undergoing physical examinations or trainee health testing. The patients attending these clinics had serum bilirubin concentrations near the mean values for the outpatient male and female populations. Most patients with RA were taking methotrexate or some other drug for RA.

Exclusion Criteria

No attempt was made to identify and exclude patients with possible liver disease, hemolytic disorders, gastrointestinal or renal obstruction, recent surgery and blood transfusions.

Laboratory Testing

Serum total bilirubin concentrations were determined in a routine manner with automated analyzers using commercial reagents. Total bilirubin was analyzed by a modification of the Jendrassik-Grof method. Serum bilirubin analyses were routinely standardized and all laboratory analyses met College American Pathology (CAP) laboratory standards.

Statistical Methods

Descriptive statistics (mean±SD, median) of serum bilirubin concentration are given for the various study populations and for serum bilirubin concentrations collected over various time periods. The Mann-Whitney U test was used to determine differences in mean serum bilirubin concentrations among the various groups.

Results

Summary Statistics

The serum bilirubin concentrations of the patients with rheumatoid arthritis, of patients attending the rheumatology service and of the control groups are shown in FIG. 4. The serum bilirubin concentrations of both men and women with rheumatoid arthritis were lower than of those in the control group ($p<0.003$ and $0.037$, respectively). The serum bilirubin concentrations of the men and women attending the rheumatology service were also lower than that of men and women in the control groups ($p<0.001$ and $0.003$, respectively). These differences were also found when the serum bilirubin of the outpatient population were used as controls ($p<0.01$). A subpopulation of the patients in the rheumatology service who were diagnosed with rheumatoid arthritis were also examined. The serum bilirubin concentrations were lower than the control for the females ($p<0.01$), but not for the males ($p<0.18$). The latter sample size though was very small ($n=2$).

Bilirubin Concentrations of Patients with Various Forms of Arthritis

The mean serum bilirubin concentrations of patients with RA, PsA, and SLE are presented in FIG. 5. The serum bilirubin concentrations for male and female patients with rheumatoid arthritis, PsA, and SLE were all similar and were in the 0.47–0.50 mg/dL range for women and 0.62–0.65 mg/dL range for men.

Inter-day Variability of Serum Bilirubin Concentrations of Patients with Arthritis Serum bilirubin concentrations on three patients with rheumatoid arthritis were determined over a 5 month to 4 year time period as shown in FIG. 6. The serum bilirubin concentrations remained low over these time periods for all three patients. Even though one male patient had a slight rise in serum bilirubin over time, the bilirubin concentrations were all low relative to those of patients without rheumatoid arthritis.

Influence of Confounding Variables

A study was made to determine if serum alanine and aspartate transaminase activities might account for the low serum bilirubin concentrations seen in individuals with rheumatoid arthritis. The alanine and aspartate transaminase activities were all in the normal range, as shown in FIG. 5.

Discussion

In this study, low serum bilirubin concentrations were found in patients with rheumatoid arthritis, as well as in patients with SLE and PsA. The low serum bilirubin levels were also found to be chronic and to be independent of the albumin concentrations and the liver function enzyme activities. The results of the study suggest that oxidative free radical production at inflammation sites might account for the low bilirubin levels. The results also support the hypothesis that low levels of bilirubin and other antioxidants might contribute to the pathogenesis of rheumatoid arthritis and that mildly elevated levels might slow the progression of rheumatoid arthritis.

For many years the bile pigment bilirubin was considered to be a toxic waste product of heme catabolism with no known function. Today, bilirubin is regarded as one of the most powerful endogenous antioxidant substances in vitro and one of the most effective physiological antioxidants in vivo. In a previous invention, one of the co-inventors showed that bilirubin is an independent risk factor for coronary artery disease (CAD) and that mildly increased levels of bilirubin are associated with a lower risk of CAD. The antioxidant properties of bilirubin are thought to be responsible for reduced risk of coronary artery disease (CAD) in individuals with mildly increased serum bilirubin.

Several recent studies have shown that patients with rheumatoid arthritis and SLE are at an increased risk of mortality due to CHD. The underlying mechanisms are not understood, however, low levels of serum bilirubin and other antioxidants could be involved in the process. The effects of chronic low bilirubin concentrations on health and mortality need to be determined. Specifically, studies are needed to determine if low serum bilirubin concentrations are the result of rheumatoid arthritis, if they cause rheumatoid arthritis, or if serum bilirubin changes along with other antioxidants and anti-inflammatory agents. Collagen-induced arthritis in mice is a widely studied animal model of inflammatory polyarthritis with similarities to rheumatoid arthritis. Recent studies have shown that the polyphenolic fraction of green tea has been shown to inhibit collagen-induced arthritis in mice. Bilirubin concentration below a certain concentration for males and females appear to indicate that the patient is at a high risk for developing rheumatoid arthritis and other inflammatory disease.

Considerable information is available on diseases and conditions that result in elevated serum bilirubin concentrations; however, little information is available on factors that might account for the low bilirubin concentrations. In rheumatoid arthritis and other inflammatory diseases, increases in oxidative and peroxidative reactions could contribute to the low serum bilirubin concentrations. There is also the possibility that other factors, such as drugs and medical treatments, might be responsible for the low serum bilirubin concentrations. Most of the drugs used for treating rheumatoid arthritis, however, have not been shown to have an effect on peroxidation reactions at least in vitro. Anticonvulsant drugs which induce liver function enzymes though have been shown to lower serum bilirubin concentrations.

Bilirubin production is controlled by two rate limiting enzymes, heme oxygenase and biliverdin reductase. Several recent studies have shown that heme oxygenase (HO) deficiency results in increased morbidity and mortality in experimental animals. The harmful effects seen in these studies were all thought to result from the inability of heme oxygenase to generate bilirubin and carbon monoxide. Activation of heme oxygenase-2 and bilirubin formation, on the other hand, has been shown to have a beneficial effect on protecting neurons against oxidative stress injury in vitro. Induction of HO-1 expression in LDL receptor knockout mice has also been shown to inhibit the formation of atherosclerotic lesions.

Bilirubin is an endogenous antioxidant that requires biliverdin reductase and an energy dependent reduction reaction for its formation. Even though the bilirubin concentrations are not high, humans produce a relatively large amount of bilirubin each day (4 mg/kg). It is estimated that a male with median weight and height would produce about 324 mg of bilirubin per day and a female would produce about 288 mg per day. This amount of daily bilirubin production is approximately 3.6 times higher for men and 3.8 times higher for women than the recommended daily intake (RDI) of vitamin C (75 mg for women, 90 for men). The bilirubin production is also 20 to 30-times the RDI of vitamin E (15 mg women, 10 mg men). As a result, endogenous antioxidants like bilirubin should be considered when evaluating the role of antioxidants in health.

A limitation of this study is a lack of information on the blood collection times, nor of whether fasting conditions were used. The blood collection times and fasting conditions in this study, however, were random for patients with and without rheumatoid arthritis. Therefore, it is unlikely that standardized blood collection procedures would have an effect on the results. Standardized blood collection conditions, such as a 12-hour fast, though would likely have decreased the biological variation in bilirubin concentration found in this study. More sensitive and specific methods for analyzing bilirubin might also indicate that patients with rheumatoid arthritis have a lower serum bilirubin concentration than those reported here.

In conclusion, patients with rheumatoid arthritis have low serum bilirubin concentrations than the control groups. The protective role of bilirubin may involve its antioxidant, anti-inflammatory and cellular protective properties. Further studies are needed to refine the determine of a prevalence of low serum bilirubin concentration among patients with rheumatoid arthritis.

Gilbert's Syndrome

Bilirubin has been shown to act as a natural antioxidant in several in vitro systems. However, a protective role has not been established in in vivo studies. Since patients with Gilbert's syndrome have a chronic and mild unconjugated hyperbilirubinemia, the study underlying this example of the present invention sought to determine if the elevated bilirubin concentrations seen in these individuals are associated with a reduction in future all-cause mortality.

Study Methods

A prospective case-control study was conducted of 385 men who subsequently died from all-causes and 839 men who were randomly chosen from survivors.

Results

The baseline fasting serum bilirubin concentration was 0.65 mg/dl for the mortality group and 0.76 mg/dl for the controls (P<0.001). An inverse association between bilirubin and all-cause mortality was found. Each mg/dl of serum bilirubin was associated with 59% decrease in all-cause mortality (95% CI: 43%–72%). This association remained significant (55% decrease, 35%–69%, p<0.001) after adjustment for age, examination year, high cholesterol, hypertension, diabetes, abnormal resting or exercise electrocardiogram, overweight, cigarette smoking and alcohol consumption. Compared to men with low bilirubin (<0.5 mg/dl), the relative risks of all-cause mortality were 0.68 (0.54–0.86, p=0.001) for men with moderate levels of bilirubin (0.5–1.0 mg/dl) and 0.51 (0.35–0.74, p<0.001) for men with elevated bilirubin concentrations (Gilbert's syndrome, bilirubin>1.0 mg/dl).

Conclusions

The prospective data showed that individuals with Gilbert's syndrome had a reduction in future all-cause mortality and that baseline fasting serum bilirubin concentrations were inversely associated with all-cause mortality.

Individuals with Gilbert's syndrome have mild, chronic unconjugated hyperbilirubinemia in the absence of liver disease or overt hemolysis. It is one of the most common syndromes found in humans and one that is frequently encountered by clinicians. Population studies indicate that up to 12 per cent of the adult population have Gilbert's syndrome. This condition has not been associated with any specific symptoms, however, complaints of lethargy, upper abdominal pain and indigestion have been reported. Although treatment with phenobarbitone has been suggested as a means to lower the bilirubin and to diminish the vague symptoms, other clinicians have suggested that therapeutic treatment is not necessary.

As earlier discussed, a co-inventors of the present invention previously found an inverse association between serum bilirubin and coronary artery disease. These findings have now been confirmed in other case control studies as well as in a prospective study. The mechanism responsible for the protective effect of bilirubin is not known, however, bilirubin has been shown to have strong antioxidant properties and to exert a cytoprotective effect in vitro. Because the long-term prognosis of individuals with moderately elevate bilirubin concentrations had not been previously studied, the study underlying this example of the present invention performed a prospective study of the association between bilirubin and all-cause mortality in a large cohort of men with Gilbert's syndrome.

Study Methods

The study is based on data from the Aerobics Center Longitudinal Study (ACLS). For the study, 18,883 men with baseline examinations during the interval from 1970 to 1987 were used and followed up to the end of 1997. Study participants came to the clinic for periodic health examinations and counseling about diet, exercise, and other lifestyle factors associated with increased risk of chronic disease. Patients with a history of cancer or cardiovascular disease at baseline were excluded. Patients with abnormal liver function tests at baseline were also excluded.

The study has been reviewed and approved annually by the Cooper Institute Institutional Review Board. All patients gave their informed consent to participate in the examination and in the follow-up study. They completed a health and medical history and underwent a physical examination by a clinic physician that included measurement of height and weight, blood chemistry analyses, measurement of blood pressure, a resting electrocardiogram (ECG) and a maximal exercise treadmill test. Details of the examination procedures are available in several prior publications.

Technicians measured height and weight with a standard physician's balance beam scale and stadiometer. Body mass index (BMI) was calculated as $kg/m^2$. Trained technicians measured blood pressure with mercury sphygmomanometers following the American Heart Association recommendations. Blood pressures were measured three times, with the lowest of the three values used in analyses. Blood samples for biochemical analyses were drawn from the antecubital vein by standard venipuncture techniques. The samples were obtained between 7 and 8 AM following an overnight fast of 12–14 hours. Total serum bilirubin from non-hemolyzed serum was analyzed with a commercial calorimetric method using diazotized sulfanilic reagent. Replicate analysis yielded a standard deviation <0.05 or a coefficient of variation <1.6%. To assess intra-patient variability in serum bilirubin, 35 patients were identified with two serum bilirubin measurements within a year. The correlation between the two measurements was 0.90. Lipids and fasting plasma glucose concentrations were determined in the Cooper Clinic laboratory with automated methods. The laboratory participates in intra- and inter-laboratory quality control programs sponsored by the Centers for Disease Control and Prevention (CDC) Lipid Standardization Program.

Mortality Surveillance

The principal method of mortality surveillance was by the National Death Index (NDI), which has been validated and widely used in population-based cohort studies. Nosologists coded the death certificates according to the International Classification of Diseases, Ninth Edition, Revised for the underlying and up to four contributing causes of death. All-cause mortality was used as the primary outcome in this analysis. CVD mortality was defined as codes 390 to 459 and cancer mortality was defined as codes 140 to 208. Only the underlying cause of death was used.

For this analysis, case subjects were those who died from any cause during follow-up. Control subjects for cases were selected randomly from among survivors who met the matching criterion of age (±5 years). Using this method, 385 all-cause deaths and 839 controls were evaluated in a prospective, nested case-control study.

Statistical Analysis

Patients were considered to have a Gilbert's syndrome if their serum bilirubin was >1 mg/dl. High serum cholesterol was defined as cholesterol concentration >6.2 mol/L (>240 mg/dl). Hypertension was defined as a history of physician-diagnosed hypertension or blood pressure $\geq 140/90$ mm Hg at the clinical examination. Diabetes was considered to be present if the patient had a history of diabetes, a history of insulin use or a fasting plasma glucose $\geq 7.0$ mmol/L ($\geq 126$ mg/dl). Current cigarette smoking was defined as self-reported "smoking now" at baseline. Overweight was defined as a BMI $\geq 25$. Alcohol intake was determined by self-reported alcohol consumption. Alcohol consumption was estimated as 1.1 grams for 1 ounce of beer, 2.7 grams for 1 ounce of wine and 15.1 grams for 1 ounce of liquor reported on the medical history questionnaire.

Conditional logistic-regression models were used that accounted for other potential variables to provide point and 95% confidence interval estimates. All reported P values are 2-sided.

Results

Baseline clinical characteristics of the 385 subjects who subsequently died and the 879 matched survivors are given in FIG. 8. Both cases and controls were free of clinical cardiovascular disease and cancer at baseline and were similar in age. As expected, cases had higher levels of total cholesterol, triglycerides, body mass index, diastolic and systolic blood pressures, prevalence of current cigarette smoking and diabetes than did the controls. The baseline serum bilirubin concentrations of the cases, however, were found to be significantly lower than those of the survivors (0.65 versus 0.76 mg/dl; P<0.0001). Bilirubin levels were not found to be associated with age in both cases (p=0.9) and controls (p=0.5).

Conditional logistic models were used to calculate the relative risk for all-cause mortality. In analysis with bilirubin as continuous variable, each mg/dl increase in bilirubin was associated with 59% decrease in all-cause mortality (p<0.0001). This association persisted after adjustment for age, examination year, high cholesterol, hypertension, diabetes, abnormal resting or exercise electrocardiogram, overweight, cigarette smoking and alcohol consumption. In addition, multivariate analysis models indicated that bilirubin is the strongest risk factor for all-cause mortality. Although serum bilirubin concentrations were different in smoking status, the association between serum bilirubin and all-cause mortality was consistently present in men with or without smoking.

To estimate the association of different bilirubin levels to all-cause mortality, case and control subjects were categorized into three categories of bilirubin: <0.5 mg/dl (low bilirubin), 0.5–1.0 mg/dl (moderate bilirubin) and >1.0 mg/dl (Gilbert's syndrome). The distribution of study subjects in cases and controls for each bilirubin category is shown in FIG. 8. After adjustment for age and examination year, the relative risks of subsequent death were 1.0, 0.68, 0.51 for the low bilirubin, moderate bilirubin, and Gilbert's syndrome groups, respectively (P for trend <0.001). An analysis was also performed on a subset with serum bilirubin concentrations ≧1.4 mg/dl (5% of the controls). This group had the lowest mortality risk relative to the group with low serum bilirubin (relative risks=0.22, 95% CI: 0.07–0.71). These associations remained significant after adjustment for age, examination year, high cholesterol, hypertension, diabetes, abnormal resting or exercise electrocardiogram, overweight, cigarette smoking and alcohol consumption, as shown in FIG. 8.

When cardiovascular disease mortality was examined, using cancer mortality and other mortality as the outcome variables, an inverse association between bilirubin and each of the three outcomes were found, as shown in FIG. 9. The association between Gilberts' syndrome and deaths from digestive disease was also examined. The group with Gilbert's syndrome were found to have only a 0.75 fold increase in risk for deaths from digestive cancer and disease. Other potential risk factors were considered such as vitamin intake, serum albumin, white blood cell count, hematocrit and hemoglobin. The association between serum bilirubin and all-cause mortality remained unchanged.

Discussion

The prospective data indicates that men with Gilbert's syndrome have a more favorable all-cause mortality than men with moderate or low bilirubin concentrations. This inverse association between baseline fasting serum bilirubin and all-cause mortality persisted after an adjustment for the conventional cardiovascular risk factors and for other potential confounders. In this study, serum bilirubin was also found to be a stronger predictor of all-cause mortality than either total cholesterol, systolic blood pressure, diastolic blood pressure or BMI. This appears to be the first prospective study to show that moderately elevated bilirubin concentrations are associated with a decreased risk of future all-cause mortality. It also appears that this is the first study on the long-term prognosis of individuals with Gilbert's syndrome.

The mechanism for the protective effect seen in individuals with Gilbert's syndrome is not known, however, hyperbilirubinaemia could be involved in several ways. Bilirubin is a naturally occurring antioxidant. As such, moderately elevated bilirubin levels may prevent DNA oxidation, thereby lowering the overall risk of cancer. Several cross-sectional studies and the prospective data of this study has that serum bilirubin concentrations are inversely associated with risk of coronary heart disease . This study was expanded to include additional end-points such as cancer mortality and all-cause mortality. It is not known whether the antioxidant properties of bilirubin are involved, if elevated bilirubin protects in some other way or if bilirubin is a marker for another risk factor. A number of studies, however, have shown that bilirubin is a strong antioxidant in vitro and that bilirubin is a more effective protector of in vitro oxidation than either vitamin E or vitamin C. In addition, a cytoprotective effect of bilirubin has been demonstrated not only in myocytes, but also in hepatocytes, erythrocytes and neurons.

In the study, Gilbert's syndrome was classified on the basis of total serum bilirubin. Under normal conditions, 96% of the total bilirubin is unconjugated. However, in individuals with heptocellular or biliary tract disease, mono- and diconjugates of bilirubin are the major forms of bilirubin. Because men with abnormal liver function were excluded from the present analysis, it is believed that the major component of total bilirubin in most of the subjects is unconjugated bilirubin.

The prevalence of Gilbert's syndrome is known to vary from one study to study. It should be noted that both dietary composition and total caloric intake can have an acute effect on bilirubin levels. For example, fasting can increase the levels of bilirubin. A normocaloric, but lipid-free diet, can also produces a response similar to that observed with complete fasting. The effect of complete fasting can also be reserved by feeding small amounts of lipids. Although fasting was noted to better distinguish Gilbert's syndrome, for many years previous studies usually used non-fasting bilirubin for the initial diagnosis for Gilbert's syndrome, which did not consider the acute effect of diet on non-fasting bilirubin, which may produce a misclassification in those studies. For example, the average non-fasting serum bilirubin concentrations in men measured in the morning were 50% higher than in men measured in the afternoon. One advantage of the present study was using standard fasting procedure with similar fasting times in each individual. The prevalence of Gilbert's syndrome in the control group in the present study (14.3%) was slightly high perhaps due to the fasting. However, when the top 5 percent of bilirubin concentration (>=1.4 mg/dl) was used as the cut point for Gilbert's syndrome, men in this category actually had the lowest risk for all-cause mortality (relative risk: 0.22).

The limitations of the study population must be taken into consideration in interpreting the results. The subjects in this report, for example, were all men and most (97%) were white. They were also from the middle and upper socioeconomic class. In spite of this, previous studies have shown associations between risk factors and cardiovascular disease, diabetes and all-cause mortality similar to that found for other populations. It remains to be determined if these results apply to women and to individuals of other races, but such an association will be reasonably expected by those of ordinary skill in the art of the invention. Diet and vitamins intake were self-reported and only reported for one time in this study. However, a study with three-day diet records was made and did not find any nutritional components in diet which was associated with fasting serum bilirubin. In addition, vitamin intake was not found to have any effect on fasting serum bilirubin.

In conclusion, this example of the present invention shows that men with Gilbert's syndrome have the best longevity and that fasting serum bilirubin concentrations were inversely associated with all-cause mortality. This finding is clinically important in that millions of men with Gilbert's syndrome may not need further medical investigation and therapy. In addition, the reduced expression of bilirubin UDP-glucuronosyltransferase 1 has been identified as the major cause of hyperbilirubinaemia. Several genes have been reported to be responsible for this reduced expression. Gene mutations in mouse enhancing resistance to ultraviolet light or reactive oxygen species has been reported to extend life span. Further prospective studies and experimental studies are needed and may provide important insight into the underlying mechanisms of hyperbilirubinaemia and may lead to a prevention and therapy for human chronic disease.

This study did not include women or older men since they were not available. Those with skill in the art, however, will see that similar results are likely to be found with these other groups. Similarly, bilirubin will likely also be valuable as a predictor of future coronary heart disease, and not just present coronary heart disease. The selection process used in this study was also different from those used in other angiographic studies. For example, the prevalence of disease in the study group was less than 18 percent, whereas the prevalence of disease in other angiographic studies was usually greater than 70 percent.

This study did not show if bilirubin has a role in preventing CAD. If the association found in this case series is confirmed by other investigations in independent study groups, then studies to elucidate a pathogenic mechanism are needed. Bilirubin is, however, an effective antioxidant, possibly protecting lipids and lipoproteins against oxidation and against plaque formation in humans. Those with skill in the art will see, therefore, that increasing bilirubin may aid in preventing CAD. Similarly, the levels of other antioxidants, such as Vitamins A, C and E, may prove useful as predictors for CAD.

Because moderately elevated levels of bilirubin appears to be protective, it can be hypothesized that any agent or drug or condition that can produce a moderate elevation in serum bilirubin may protect against cardiovascular disease, certain types of cancer, rheumatoid arthritis, cardiovascular mortality, cancer mortality and all-cause mortality. A search has been made of the literature to find drugs that might produce slight increases in bilirubin, but not high levels as with drugs that damage the liver. Aspirin is a candidate. Likewise, some of the porphyrins can increase bilirubin by inhibiting heme oxygenase, a key enzyme in bilirubin synthesis. Other approaches would be to activate heme oxygenase so that more bilirubin is synthesized. These drugs could then be used as therapeutic agents for increasing serum bilirubin concentrations and protecting an individual against arthritis, cardiovascular disease, and cancer.

The disclosed new method for predicting tests for determining the risk of future onset of various diseases successfully demonstrates the use of serum bilirubin as a determining factor. Although the disclosed methods are specialized, their teachings will find application in other areas where careful analysis of existing factors may reveal their suitability as predictive factors for medical diseases, mechanical devices and industrial processes.

It is understood that various modifications to the invention as described may be made, as might occur to one with skill in the field of the invention, within the scope of the claims. Therefore, all embodiments contemplated have not been shown in complete detail. Other embodiments may be developed without departing from the spirit of the invention or from the scope of the claims.

We claim:

1. A method for characterizing the risk of rheumatoid arthritis for an individual, comprising the steps of:
   (a) obtaining the level of the individual's serum total bilirubin;
   (b) comparing the obtained level to a threshold level for serum total bilirubin of near or below 0.57 mg/dl for males and near or below 0.40 for females; and,
   (c) characterizing from the comparison the risk of rheumatoid arthritis for the individual, wherein an obtained level below the threshold level indicates that the individual is at increased risk for rheumatoid arthritis.

* * * * *